United States Patent [19]

Smith

[11] 4,364,377

[45] Dec. 21, 1982

[54] MAGNETIC FIELD HEMOSTASIS

[75] Inventor: Frederic W. Smith, Portland, Oreg.

[73] Assignee: Walker Scientific, Inc., Worcester, Mass.

[21] Appl. No.: 230,621

[22] Filed: Feb. 2, 1981

Related U.S. Application Data

[63] Continuation of Ser. No. 9,227, Feb. 2, 1979, abandoned.

[51] Int. Cl.³ .............................................. A61B 17/12
[52] U.S. Cl. ...................................... 128/1.5; 128/325
[58] Field of Search ........................... 128/1.3, 1.5, 325

[56]  References Cited

U.S. PATENT DOCUMENTS

| | | | |
|---|---|---|---|
| 3,095,877 | 7/1963 | Rowan | 128/325 |
| 3,411,506 | 11/1968 | Velasco | 128/325 |
| 3,723,244 | 3/1973 | Breillatt, Jr. | 128/325 |
| 3,765,419 | 10/1973 | Usher | 128/325 |
| 3,794,041 | 2/1974 | Frei' et al. | 128/1.3 |
| 4,005,699 | 2/1977 | Bucalo | 128/1.3 |

OTHER PUBLICATIONS

Newbower, "IEEE Transactions on Magnetics", vol. MAG. 9, No. 3, Sep. 1973, pp. 447-450.
Roth, Journal of the American Medical Association, May 5, 1969, vol. 208, No. 5, p. 781.

*Primary Examiner*—William E. Kamm
*Attorney, Agent, or Firm*—Kenway & Jenney

[57]  ABSTRACT

Disclosed is a method for staunching blood flow from an acutely bleeding gastrointestinal lesion. The method comprises introducing, into the gastrointestinal tract, a tamponading mass having ferromagnetic properties. A suitable tamponading mass is a mixture of finely divided iron particles and vegetable oil which may be introduced through an endoscopic catheter. Once in the gastrointestinal tract, the tamponading mass is moved as necessary to cover and press upon the bleeding lesion by a magnetic field generated outside the body, e.g. by an electromagnet. The positioning is under the direct visual control of the endoscopist.

18 Claims, 2 Drawing Figures

MAGNETIC FIELD HEMOSTASIS

This is a continuation of application Ser. No. 9,227, filed Feb. 2, 1979 now abandoned.

BACKGROUND OF THE INVENTION

This invention relates to a method of stopping gastrointestinal bleeding and more particularly to such a method which employs a ferromagnetic tamponading mass pressed against a bleeding gastrointestinal lesion by an externally generated magnetic field.

The difficulties of stopping the bleeding of gastrointestinal lesions such as acutely bleeding ulcers is well known. Although several techniques are presently used to control bleeding, no one of them is without serious deficiencies. For example, procedures to stem the blood flow by cauterizing the lesion with heated probes or lasers introduced into the gastrointestinal tract using gastrointestinal fiberscopes may destroy healthy tissue near the lesion. Furthermore, these techniques require precise identification of the bleeding point and a relatively clear, blood free field. Another technique involves coating the lesion with a tissue cement. Again, accurate placement and a clean, blood-free field are required. Various drugs are also known which have limited utility in controlling, but not completely stopping, blood flow from acutely bleeding gastrointestinal ulcers or other actively bleeding gastrointestinal lesions.

It is an object of the present invention, therefore, to provide a method to staunch the blood flow from acutely bleeding gastric ulcers or other acutely bleeding lesions.

It is a further object to provide such a method which requires neither a clean, blood-free field nor the accurate positioning of an endoscopic catheter in relation to the lesion in order to be effective.

A still further object is to provide a method for stopping the blood flow from a gastric ulcer or other actively bleeding gastrointestinal lesion which is easier to implement than currently known procedures.

SUMMARY OF THE INVENTION

In the process for stopping gastrointestinal bleeding according to the present invention, there is provided a tamponading mass which has ferromagnetic properties. This mass may be introduced into the gastrointestinal tract through an endoscope catheter under the direct visual control of the endoscopist. The ferromagnetic tamponading mass is then biased within the gastrointestinal tract to cover and press upon a bleeding lesion by means of an externally generated magnetic field. Typically, the pressure of the tamponading mass on the lesion has been found to stop completely its bleeding.

In a preferred embodiment, the tamponading mass comprises a mixture of finely divided particles with ferromagnetic properties such as iron or iron oxide and a viscous liquid such as vegetable oil. This mixture may also contain clotting factors such as thrombin, chemical cautery agents or tissue cements to aid the clotting process. The tamponading mass may be introduced into the gastrointestinal tract through an endoscopic catheter.

In another important embodiment, the tamponading mass comprises particles of a ferromagnetic material, such as finely divided iron particles, each particle being encased within a biologically inert covering, for example, silicone rubber.

In yet another embodiment, a latex baloon filled with a ferromagnetic material such as iron powder is used as the tamponading mass, obviating thereby the need for a viscous suspending fluid.

Because the tamponading mass is moved or biased by the externally generated magnetic field so as to cover the bleeding lesion, it is unnecessary to position precisely the catheter which delivers the ferromagnetic mass into the gastrointestinal tract. In addition, it is unnecessary to clear blood away from the lesion before the tamponading mass is applied; the presence of blood has been found not to interfere with hemostasis.

BRIEF DESCRIPTION OF THE DRAWING

The invention disclosed herein will be better understood with reference to the accompanying drawing of which.

DESCRIPTION OF THE PREFERRED EMBODIMENTS

Figure 1:
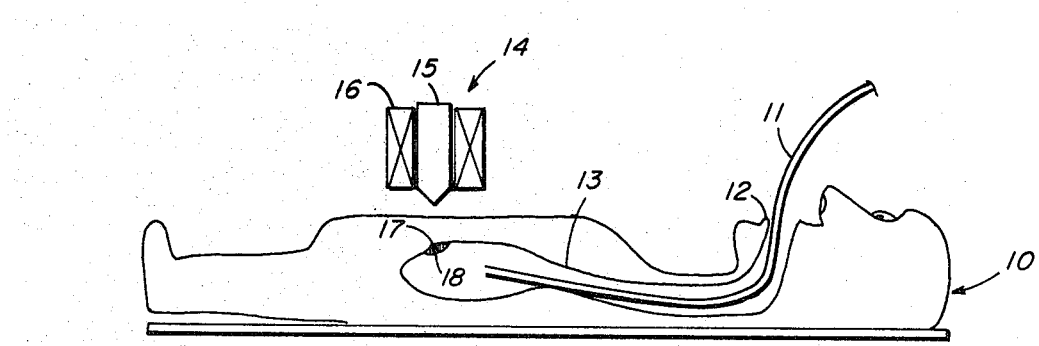
FIG. 1 is a simplified schematic diagram illustrating a preferred embodiment of the method disclosed herein; and, FIG. 2 is a simplified schematic diagram of another embodiment of the method disclosed herein.

Referring first to FIG. 1, a patient 10 is shown with an endoscopic catheter 11 inserted through the mouth 12 and into the gastrointestinal tract 13. Electromagnet 14, comprising an iron core pole piece 15 surrounded by windings 16, is positioned above the patient 10 and over an acutely bleeding ulcer or lesion 17. The windings 16 may be eliminated if the piece 15 is a permanent magnet. The magnet 14 is supported by conventional means (not shown) which allows the magnet's position to be adjusted as necessary.

A slurry or "mud" 18 made of a mixture of finely divided iron particles and a vegetable oil is injected into the gastrointestinal tract 14 through the catheter 11 by conventional means such as a piston and cylinder (not shown) and is moved to cover and press upon the lesion 17 by magnet 14. The tamponading "mud" 18 may also contain a clotting factor such as thrombin to facilitate hemostasis. The magnetic field is kept on for a period sufficient for a firmly adherent clot to form over the lesion 17. Typically, fifteen minutes time is adequate. When the field is turned off, the "mud" 18 disperses and is eliminated by the body.

Figure 2:
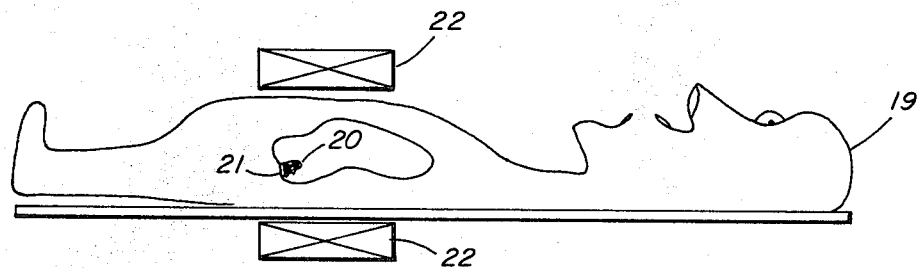

FIG. 2 illustrates an arrangement for pressing a tamponading mass 20 such as a ferromagnetic mass encased within a biologically inert covering along the longitudinal axis of patient 19 against a lesion 21. To accomplish this, the patient 19 is positioned within the windings of an air core magnet 22 so that magnetic force lines are substantially parallel to the longitudinal axis of the patient 19 thereby pressing the tamponading mass 20 against lesion 21.

Referring again to FIG. 1, a suitable magnet 14 is model X-5242 manufactured by Walker Scientific of Worcester, Massachusetts. This magnet has a power output of 8.5 kilowatts and a maximum field intensity at the tip of the pole piece 15 of 10,000 Gauss. One suitable tamponading "mud" 18 is a mixture in equal parts by volume of 100 mesh iron powder with a vegetable oil such as Crisco ® creating a mass having the consistency of cold cream. 500 NIH units of thrombin per cubic centimeter of tamponading mass may also be included in the mixture to facilitate clot formation. Approximately 10 cubic centimeters of the "mud" 18 will cover a one square inch area, and with the pole piece 15 of magnet 14 three inches from lesion 17, the "mud" 18 exerts a force on the lesion 17 of 0.4 pounds, thereby generating pressures of between 20 and 40 millimeters of mercury. Maintaining this pressure for approximately 15 minutes time is sufficient for hemostasis to occur.

Although finely divided iron powder mixed with vegetable oil is preferred as the tamponading mass, it is to be stressed that other ferromagnetic materials and alloys are suitable, e.g., magnetic oxides of iron and Alnico ®. In addition to vegetable oil, other viscous liquids may be used successfully as a suspending medium for the ferromagnetic material. Representative suitable suspending liquids include starch gel, liquid silicone, glycerine and glycerine-based gels.

The invention disclosed herein has proved to be a highly effective method for stopping bleeding from experimentally produced acute gastrointestinal lesions in the dog. This method of treatment is potentially safer than other techniques which are currently under evaluation and does not require, as do other techniques, a clear, blood-free field.

Other important applications for the present technique are to be noted. For example, the addition of an appropriate antibiotic to the ferromagnetic tamponading mass provides an effective method of treating infection. In such a situation, the antibiotic-containing tamponading mass is held over an infected area within the gastrointestinal tract by means of an externally generated magnetic field for a time sufficient for the antibiotic to act. As an illustration, esophogeal candidiasis may be treated by adding the highly effective drug clotrimazole to the tamponading mass; the local application of this drug to the infected area minimizes systemic side effects expected with other means of administration. Furthermore, the addition of steroids to the tamponading mixture makes it possible to manage more effectively inflammatory conditions such as, for example, ulcerative colitis.

As various changes could be made in the above preferred embodiments without departing from the scope of the invention, it is to be understood that all matter contained in the above description or shown in the accompanying drawing shall be interpreted as illustrative and not in a limiting sense.

I claim:

1. Process for staunching bleeding at a lesion located in a comparatively large body cavity such as the gastrointestinal tract comprising the steps of:
   (1) providing a liquid tamponading mass of a large volume that covers said lesion, said liquid mass being formed of ferromagnetic particles suspended in said large volume of a viscous liquid;
   (2) introducing said mass into the gastrointestinal tract; and
   (3) biasing said mass to cover and to press upon a bleeding lesion within said gastrointestinal tract by externally generated magnetic field means that acts upon said ferromagnetic particles, said biasing acting to hold said liquid mass in position over said lesion and to staunch the bleeding at said lesion.

2. The process of claim 1 wherein said particles are iron and said liquid is oil.

3. The process of claim 1 wherein said tamponading mass is encased within a biologically inert covering material.

4. The process of claim 1 wherein said introducing is accomplished with an endoscopic catheter.

5. The process of claim 1 wherein said externally generated magnetic field means comprises an electromagnet.

6. The process of claim 1 wherein said externally generated magnetic field means comprises a permanent magnet.

7. The process of claim 1 wherein said tamponading mass includes at least one blood clotting factor.

8. The process of claim 7 wherein said clotting factor is thrombin.

9. The process of claim 1 wherein said tamponading mass includes tissue cement.

10. The process of claim 1 wherein said tamponading mass includes a chemical cautery agent.

11. The process of claim 1 wherein said particles are iron oxide.

12. The process of claim 1 wherein said particles are iron covered with silicone rubber.

13. The process of claim 1 wherein said viscous liquid is starch gel.

14. The process of claim 1 wherein said viscous liquid is liquid silicone.

15. The process of claim 1 wherein said viscous liquid is glycerine.

16. The process of claim 1 wherein said viscous liquid is a glycerine-based gel.

17. Process for stopping bleeding at a lesion located in a comparatively large body cavity such as the gastrointestinal tract comprising the steps of:
   (1) providing a liquid tamponading mass of a large volume that covers said lesion, said liquid mass being formed of a mixture of finely divided iron particles suspended in said volume of oil;
   (2) introducing said mass into the gastrointestinal tract through an endoscopic catheter;
   (3) moving said mass to cover said lesion by external electromagnet means; and
   (4) biasing said mass to press upon said lesion by electromagnet means to stop the bleeding.

18. The process of claim 17 wherein said tamponading mass includes thrombin.

* * * * *